United States Patent
Yoshikawa et al.

(10) Patent No.: US 8,260,560 B2
(45) Date of Patent: Sep. 4, 2012

(54) FUEL PROPERTY DETERMINING APPARATUS

(75) Inventors: Koji Yoshikawa, Obu (JP); Hisashi Kino, Ichinomiya (JP); Naoaki Matsubara, Obu (JP)

(73) Assignee: Aisan Kogyo Kabushiki Kaisha, Obu-Shi (JP)

( * ) Notice: Subject to any disclaimer, the term of this patent is extended or adjusted under 35 U.S.C. 154(b) by 397 days.

(21) Appl. No.: 12/728,738

(22) Filed: Mar. 22, 2010

(65) Prior Publication Data

US 2010/0241362 A1  Sep. 23, 2010

(30) Foreign Application Priority Data

Mar. 23, 2009  (JP) ................................. 2009-070927

(51) Int. Cl.
*G01N 31/00* (2006.01)
(52) U.S. Cl. ........................................................ 702/24
(58) Field of Classification Search .................... 702/24, 702/182–185
See application file for complete search history.

(56) References Cited

U.S. PATENT DOCUMENTS

| 2008/0162017 | A1* | 7/2008 | Nagata et al. ................. 701/103 |
| 2010/0020325 | A1* | 1/2010 | Osaki et al. ................... 356/436 |
| 2010/0036587 | A1 | 2/2010 | Kato et al. | |
| 2012/0047992 | A1* | 3/2012 | Sasai ........................... 73/23.32 |

FOREIGN PATENT DOCUMENTS

| JP | H5-223723 A | 8/1993 |
| JP | 2004-191110 A | 7/2004 |
| JP | 2007-147585 A | 6/2007 |
| JP | 2008-180103 A | 8/2008 |

* cited by examiner

*Primary Examiner* — Edward Raymond
(74) *Attorney, Agent, or Firm* — J-Tek Law PLLC; Jeffrey D. Tekanic

(57) ABSTRACT

A fuel property determining apparatus may comprise a first sensor and second sensor. The first sensor may detect a concentration of an alcohol contained in fuel. The second sensor may detect a vapor pressure of the target fuel. The fuel property determining apparatus may further comprise a memory and a processor. The memory may store first data for determining a "heavy/light gravity—vapor pressure" relationship based on the concentration of the alcohol. The processor may determine the fuel property of the target fuel based on the first data stored in the memory, the alcohol concentration detected by the first sensor, and the vapor pressure detected by the second sensor.

14 Claims, 9 Drawing Sheets

FIG. 12

| Vapor Pressure \ Alcohol Concentration | 0% | 10% | ...... | 100% |
|---|---|---|---|---|
| Fuel A (Heavy or Light Quality is a%) | $a_0$ | $a_{10}$ | | $a_{100}$ |
| Fuel B (Heavy or Light Quality is b%) | $b_0$ | $b_{10}$ | | $b_{100}$ |
| Fuel C (Heavy or Light Quality is c%) | $c_0$ | $c_{10}$ | | $c_{100}$ |

FUEL PROPERTY DETERMINING APPARATUS

CROSS-REFERENCE TO RELATED APPLICATION

This application claims priority to Japanese Patent Application No. 2009-70927 filed on Mar. 23, 2009, the contents of which are hereby incorporated by reference into the present application.

TECHNICAL FIELD

The present teachings relate to an apparatus for determining a property of fuel supplied to an internal combustion engine (e.g., an automobile engine). Particularly, the present teachings relate to an apparatus for determining the fuel property of alcohol-containing fuel.

DESCRIPTION OF THE RELATED ART

In order to combust fuel supplied to an internal combustion engine at an appropriate air-fuel ratio, it is necessary to accurately determine a property of the fuel. Especially when using alcohol-containing fuel, an alcohol concentration thereof needs to be taken into consideration, as the theoretical air-fuel ratio of the alcohol is different than that of the gasoline. Japanese Patent Application Publication No. 2008-180103 discloses an apparatus for determining the property of alcohol-containing fuel. In this apparatus, two sensors are attached to a fuel path through which the fuel discharged from a fuel pump flows. One of the sensors detects a heavy/light gravity of the fuel, while the other sensor detects the alcohol concentration of the fuel. Then, the property of the fuel is determined based on the detected heavy/light gravity and the detected alcohol concentration, and the injection amount of the fuel supplied to the internal combustion engine is determined. The heavy/light gravity herein refers to a degree of composition within the fuel. For example, fuel having high heavy/light gravity may be referred to as "heavy fuel" or "having high density", and fuel having low heavy/light gravity may be referred to as "light fuel" or "having low density".

SUMMARY

In the conventional apparatus described above, the property of the fuel is determined based on the detected heavy/light gravity and the detected alcohol concentration. Therefore, both the heavy/light gravity of the fuel and the alcohol concentration of the fuel need to be detected with a high degree of accuracy, in order to determine the property of the fuel accurately. However, the conventional apparatus detects a refractive index of the fuel, specifies a density of the fuel from this refractive index, and calculates the heavy/light gravity of the fuel from the specified fuel density. For this reason, this apparatus is not capable of calculating the heavy/light gravity of the fuel accurately. That is, because the refractive index of the fuel changes less significantly than the fuel density, the density of the fuel cannot be specified accurately from the refractive index of the fuel. Hence, the heavy/light gravity cannot be calculated accurately, and, as a result, the property of the fuel cannot be determined with a high degree of accuracy.

It is an object of the present teachings to provide a technology for determining the property of target fuel accurately.

In one aspect of the present teachings, an apparatus may comprise a first sensor, a second sensor, a memory, and a processor. The first sensor detects a concentration of an alcohol contained in target fuel. The second sensor detects a vapor pressure of the target fuel. The memory stores data for determining a "heavy/light gravity—vapor pressure" relationship based on the concentration of the alcohol. The processor determines fuel property of the target fuel based on the data stored in the memory, the concentration of the alcohol detected by the first sensor, and the vapor pressure detected by the second sensor.

With this apparatus, the memory stores the data for determining the "heavy/light gravity—vapor pressure" relationship based on the concentration of the alcohol. Therefore, when the first sensor detects the alcohol concentration, the processor can determine the "heavy/light gravity—vapor pressure" relationship of the target fuel from this data. Thus, when the second sensor detects the vapor pressure of the target fuel, the processor can determine the heavy/light gravity of the target fuel based on the "heavy/light gravity—vapor pressure" relationship and the detected vapor pressure. Here, the sensitivity of the first sensor is higher than the sensitivity of the second sensor. Thus, the first sensor can detect the alcohol concentration of the target fuel more accurately. Consequently, the "heavy/light gravity—vapor pressure" of the target fuel can also be determined accurately. Then, the heavy/light gravity can be determined accurately from the accurately determined "heavy/light gravity—vapor pressure" relationship and the detected vapor pressure. Because the alcohol concentration and the heavy/light gravity of the target fuel are determined with a high degree of accuracy, the property of the target fuel can be determined precisely.

Other objects, features and advantages of the present teachings will be readily understood by the following detailed description together with the accompanying drawings and claims. Of course, the additional features and aspects disclosed herein may be utilized singularly or, in combination with the above-described aspects and features.

BRIEF DESCRIPTION OF THE DRAWINGS

FIG. 12 is a diagram showing one example of data stored in a memory of the ECU.

DESCRIPTION OF THE PREFERRED EMBODIMENTS

First Embodiment

Figure 1:
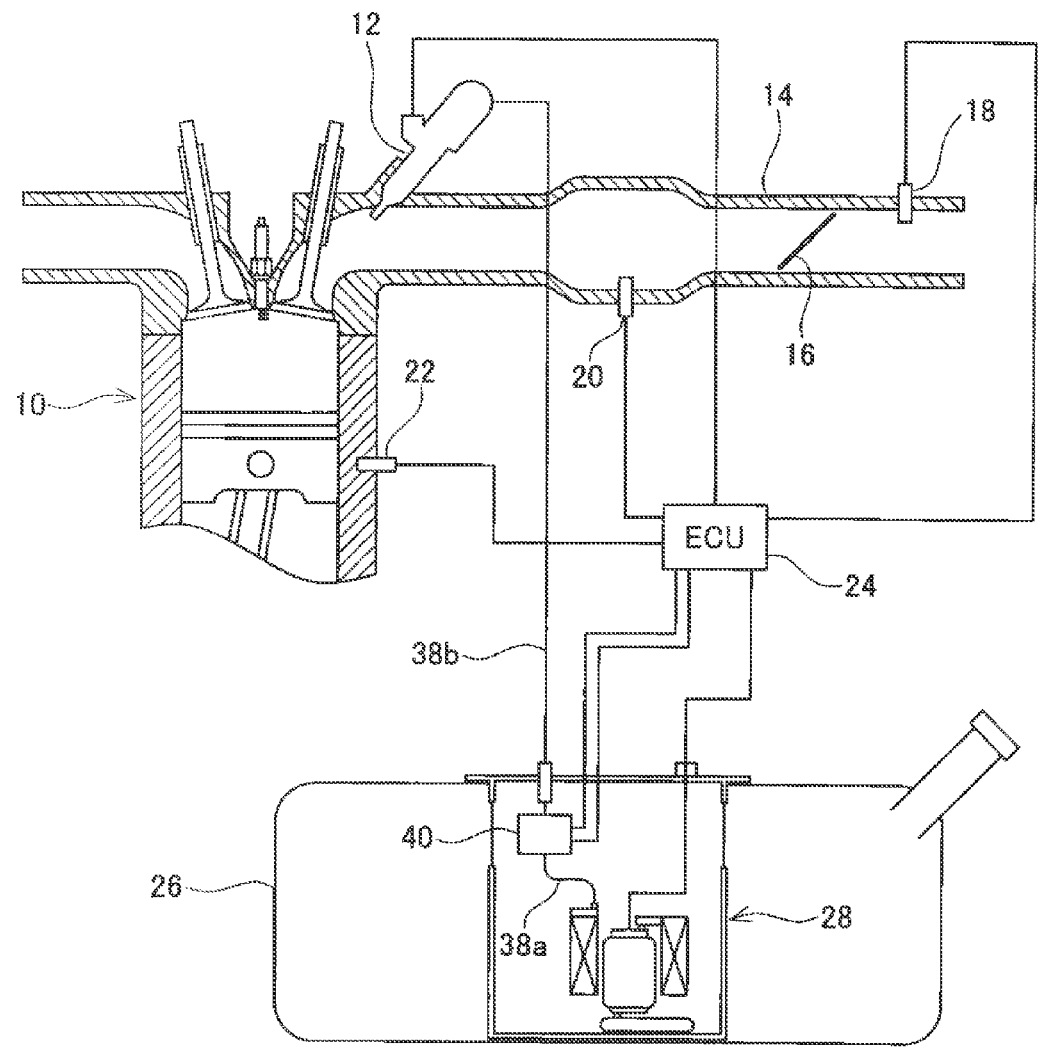
FIG. 1 is a diagram showing a configuration of a fuel supply system according to a first embodiment of the present teachings.

A fuel property determining apparatus according to a first embodiment will be explained with reference to the drawings. First of all, a configuration of a fuel supply system of an internal combustion engine equipped with the fuel property determining apparatus will be described. As shown in FIG. 1, the fuel supply system of the present embodiment has a fuel tank 26 for retaining fuel. The fuel retained in the fuel tank 26 contains alcohol (i.e., ethanol in the present embodiment). This fuel hereinbelow may also be referred to as "target fuel". A fuel supply device 28 is disposed in the fuel tank 26. The fuel supply device 28 increases the pressure of the fuel within the fuel tank 26 and discharges the pressurized fuel to the outside of the fuel tank 26. One end of a fuel supply path (38a, 38b) is connected to the fuel supply device 28. The other end of the fuel supply path (38a, 38b) is connected to an injector 12. The fuel discharged from the fuel supply device 28 is supplied to the injector 12 via the fuel supply path (38a, 38b).

The injector 12 injects the fuel supplied from the fuel supply device 28. The injector 12 is attached to an intake manifold 14. The intake manifold 14 is attached to the intake side of an engine 10. A throttle valve 16 is provided at the intake manifold 14. The throttle valve 16 adjusts the quantity of air flowing through the intake manifold 14. By controlling the throttle valve 16, the amount of air supplied to the engine 10 is controlled. An intake air temperature sensor 18 is disposed on the upstream side of the throttle valve 16, and a flow rate sensor 20 is disposed on the downstream side of the throttle valve 16. The intake air temperature sensor 18 detects the temperature of air flowing inside the intake manifold 14. The flow rate sensor 20 detects the flow rate of the air flowing within the intake manifold 14. A knock sensor 22 for detecting an engine knock is attached to the engine 10. Each of the sensors 18, 20, 22 is connected electrically to an ECU 24.

The output from each of the sensors 18, 20, 22 and the output from an alcohol concentration detection sensor 40 are input to the ECU 24. The ECU 24 calculates the concentration of the alcohol contained in the fuel, based on the output of the alcohol concentration detection sensor 40. The ECU 24 also controls the flow rate of the fuel injected from the injector 12 and the timing of injecting the fuel from the injector 12, based on the calculated alcohol concentration and the output of each of the sensors 18, 20, 22. The process for calculating the alcohol concentration using the ECU 24 is described hereinafter.

Figure 2:
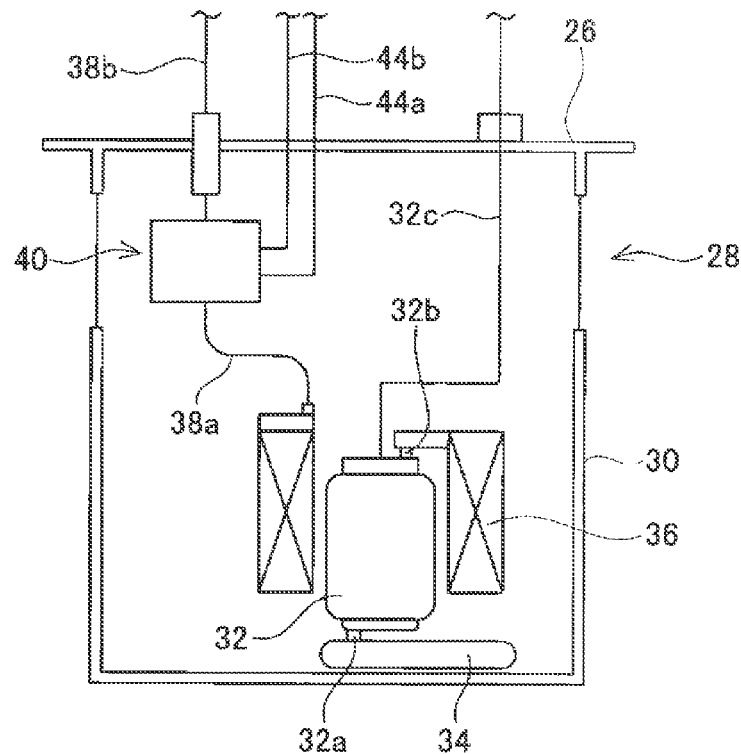
FIG. 2 is a diagram showing an enlargement of a configuration within a fuel tank.

Next, the fuel supply device 28 disposed within the fuel tank 26 will be described. As shown in FIG. 2, the fuel supply device 28 comprises a reservoir cup 30 and a fuel pump 32 disposed within the reservoir cup 30. The reservoir cup 30 temporarily retains the fuel of the fuel tank 26. The fuel pump 32 is connected to the ECU 24 by a wiring 32c. When electric power is supplied from the ECU 24 to the fuel pump 32 via the wiring 32c, the fuel pump 32 suctions the fuel within the reservoir cup 30, increases the pressure of the suctioned fuel, and discharges the pressurized fuel. A suction filter 34 is attached to a suction port 32a of the fuel pump 32. A high-pressure filter 36 is attached to a discharge port 32b of the fuel pump 32. Therefore, the fuel, from which foreign matters are removed by the suction filter 34, is suctioned into the fuel pump 32, and the fuel discharged from the fuel pump 32 is further subjected to removal of foreign matters by the high-pressure filter 36. One end of the fuel supply path 38a is connected to the high-pressure filter 36. The other end of the fuel supply path 38a is connected to the alcohol concentration detection sensor 40. One end of the fuel supply path 38b is connected to the alcohol concentration detection sensor 40, and the other end of the fuel supply path 38b is connected to the injector 12 (see FIG. 1). Therefore, the fuel, from which the foreign matters are removed by the high-pressure filter 36, flows to the alcohol concentration detection sensor 40 via the fuel supply path 38a, and further flows to the injector 12 from the alcohol concentration detection sensor 40 via the fuel supply path 38b. Note that because the alcohol concentration detection sensor 40 is supplied with the fuel from which the foreign matters are removed by the high-pressure filter 36, the concentration of the alcohol contained in the fuel can be detected with a high degree of accuracy. Moreover, by disposing the alcohol concentration detection sensor 40 within the fuel tank 26, the influence of the ambient temperature on detecting accuracy can be reduced.

Figure 3:
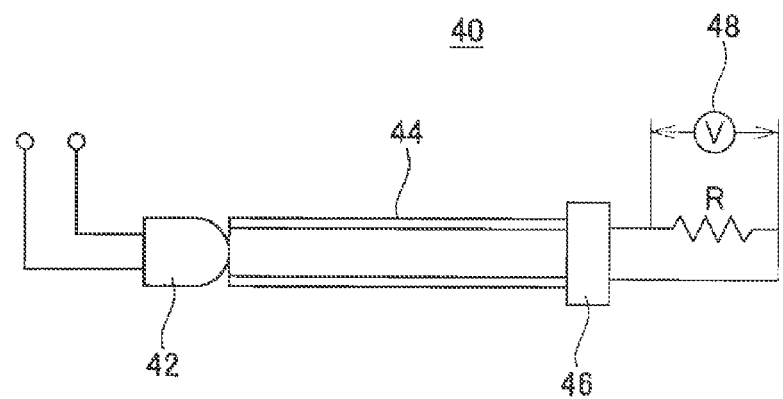
FIG. 3 is a diagram showing a configuration of an alcohol concentration detector.
Figure 4:
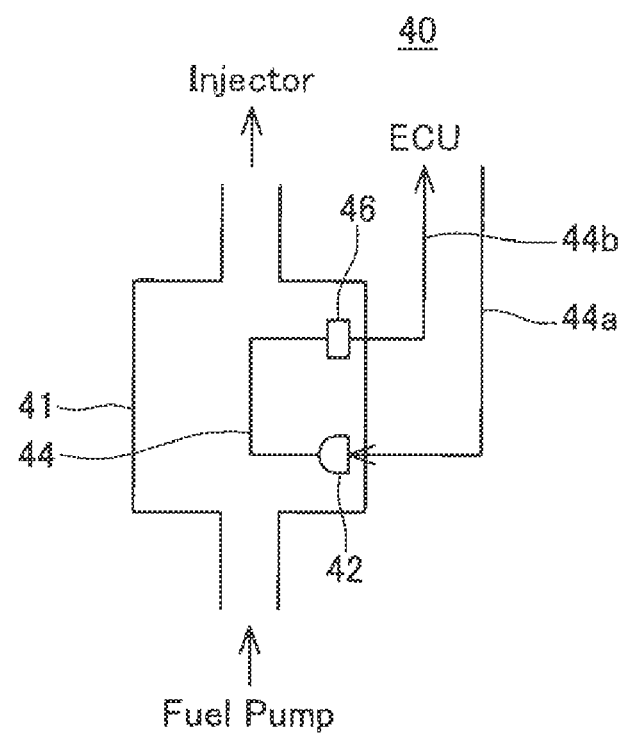
FIG. 4 is a schematic diagram showing a state in which the alcohol concentration detector is attached.

As shown in FIGS. 3 and 4, the alcohol concentration detection sensor 40 comprises an LED 42, optical fiber 44, and photodiode 46. As shown in FIG. 4, the LED 42, the optical fiber 44 and the photodiode 46 are disposed within a housing 41 forming a fuel flow path. For this reason, while the fuel is discharged from the fuel pump 32, the LED 42, the optical fiber 44 and the photodiode 46 are immersed in the fuel.

The LED 42 is connected to the ECU 24 by a wiring 44a. The ECU 24 controls the on/off of the LED 42. When the LED 42 is turned on, the LED 42 emits light. The LED 42 is disposed in a position near one of end surfaces of the optical fiber 44. Thus, the light emitted from the LED 42 enters this end surface of the optical fiber 44. Note that in the present embodiment, the LED 42 is used as a light source, but other light source can be used as an alternate (e.g., a laser light source).

Figure 5:
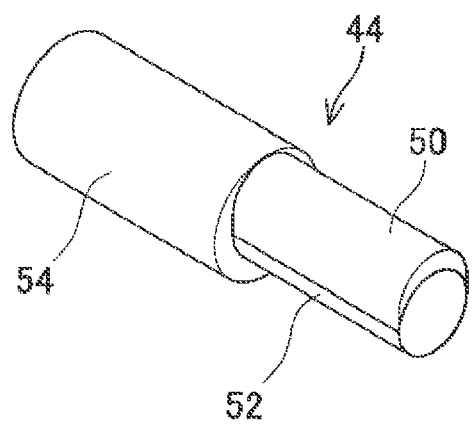
FIG. 5 is a diagram showing a state in which a gold thin film is formed on a surface of the core of optical fiber.

The optical fiber 44 propagates the light entering the one end surface to the other end surface. As shown in FIG. 5, the optical fiber 44 has a core 52 and clad 54. The core 52 and the clad 54 are made from quartz glass or plastic with high transmittance to the light. The refractive index of the core 52 is larger than the refractive index of the clad 54. Therefore, most of the light that has entered the optical fiber 44 is propagated through the core 52. The clad 54 is provided on an outer circumferential surface of the core 52. A part of the clad 54 is removed. In the removed part of the clad 54, the core 52 is directly exposed to an internal space of the housing 41. In the part where the core 52 is exposed to the internal space of the housing 41, a thin film 50 made of gold (to be referred to as "gold thin film 50" hereinafter) is formed on a surface of the core 52. In the present embodiment, the gold thin film 50 is formed on half surface on one side of the core 52 (i.e., surface on the upper side of FIG. 5)). The gold thin film 50 can be formed by means of a vacuum deposition method. The gold thin film 50 is formed to have a thickness of 1 to 200 nm at which a surface plasmon resonance phenomenon occurs easily.

Note that, although gold is used in the present embodiment in order to generate the surface plasmon resonance phenomenon, other types of metals (e.g., silver, copper, aluminum, etc.) can be used as the material of the thin film formed on the surface of the core 52. As a further alternate, a thin film having gold and these metals stacked together can be used as well.

The photodiode 46 receives the light propagated through the optical fiber 44, and converts the received light into current. The current converted by the photodiode 46 is proportional to the intensity of the received light. This current is converted into voltage by a resistor R. The voltage converted by the resistor R is measured by a voltmeter 48. The voltage measured by the voltmeter 48 is input to the ECU 24 via a wiring 44b.

Figure 6:
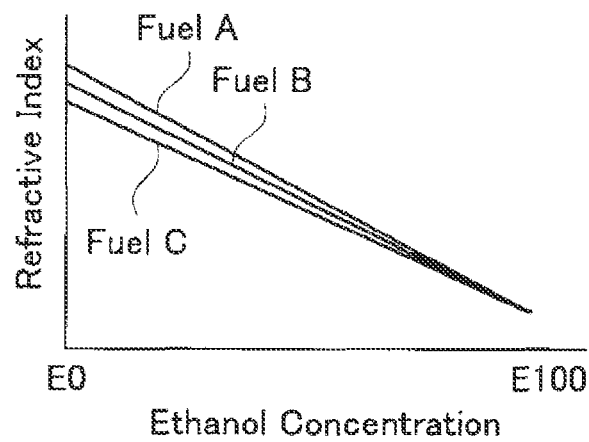
FIG. 6 is a graph showing a relationship between the refractive index and the alcohol concentration (ethanol concentration).

The ECU 24 determines the refractive index of the fuel from the voltage measured by the voltmeter 48, and then determines the concentration of the alcohol contained in the fuel from this refractive index. That is, because the optical fiber 44 (i.e., core 52) is immersed in the fuel, the gold thin film 50 on the core 52 is in contact with the fuel. Thus, when the light enters the optical fiber 44 (i.e., core 52), the surface plasmon resonance phenomenon is caused by the gold thin film 50, and a part of the light entering the optical fiber 44 is absorbed. The intensity of the light absorbed by the surface plasmon resonance phenomenon varies depending on the refractive index of the fuel that is in contact with the gold thin film 50. Therefore, the ECU 24 determines the refractive index of the fuel from the voltage measured by the voltmeter 48 (i.e., the ECU 24 determines the intensity of the light received by the photodiode 46). The relationship shown in FIG. 6 is established between the refractive index of the fuel and the alcohol concentration of the fuel. In FIG. 6, the refractive index as a function of alcohol concentration decreases as the alcohol concentration increases. That is, the higher the alcohol concentration is, the lower the refractive index becomes. Thus, the ECU 24 determines the alcohol concentration of the fuel from the determined refractive index.

In the fuel property determining apparatus of the present embodiment, the gold thin film 50 is formed on the surface of the core 52 of the optical fiber 44, and a part of the light propagated through the core 52 is absorbed by the surface plasmon resonance phenomenon. As a result, the intensity of the light received by the photodiode 46 changes significantly as the refractive index of the fuel changes, whereby the refractive index of the fuel can be determined precisely. Consequently, the alcohol concentration of the fuel can also be determined accurately.

Second Embodiment

Next, a fuel property determining apparatus according to a second embodiment of the present teachings will be described. Unlike the fuel property determining apparatus of the first embodiment, different types of fuel may be used as the fuel of the internal combustion engine (i.e., fuel with different heavy/light gravity), and the fuel property determining apparatus of the second embodiment is capable of detecting the alcohol concentration in accordance with the type of fuel used. Note that the hardware configuration of the fuel property determining apparatus is same as the one of the first embodiment, and thus the overlapping description is omitted.

In the second embodiment, three types of fuel A, B, C with different heavy or light qualities are used. As is clear from FIG. 6, "refractive index—alcohol concentration" properties (relationships) of the fuels A, B, C are substantially the same. In other words, even when the heavy or light qualities of the fuels are different, the "refractive index—alcohol concentration" relationships of the fuels are substantially the same. Therefore, the ECU stores one of the "refractive index—alcohol concentration" relationships of the fuel types A, B, C. Specifically in this embodiment, the "refractive index—alcohol concentration" relationship of the fuel type B is stored beforehand. This is because the "refractive index—alcohol concentration" relationship of the fuel type B shows a substantially intermediate property between the "refractive index—alcohol concentration" relationship of the fuel type A and the "refractive index—alcohol concentration" relationship of the fuel type C.

When the ECU determines the refractive index of the fuel from the voltage output from the photodiode of the alcohol concentration detection sensor, the ECU reads the stored "refractive index—alcohol concentration" relationship first. Then, the ECU determines the alcohol concentration of the fuel from the read "refractive index—alcohol concentration" relationship and the determined refractive index. As a result, even when the fuel types A, B, C (heavy or light qualities of the fuels) are different, the concentration of the alcohol contained in the fuel can be detected accurately.

Third Embodiment

Next, a fuel property determining apparatus according to a third embodiment will be described. Unlike the fuel property determining apparatus of the first embodiment, the fuel property determining apparatus of the third embodiment has a compensation optical fiber separate from the optical fiber having the gold thin film formed thereon. The rest of the configuration is same as that of the first embodiment, and thus the overlapping description is omitted.

Figure 7:
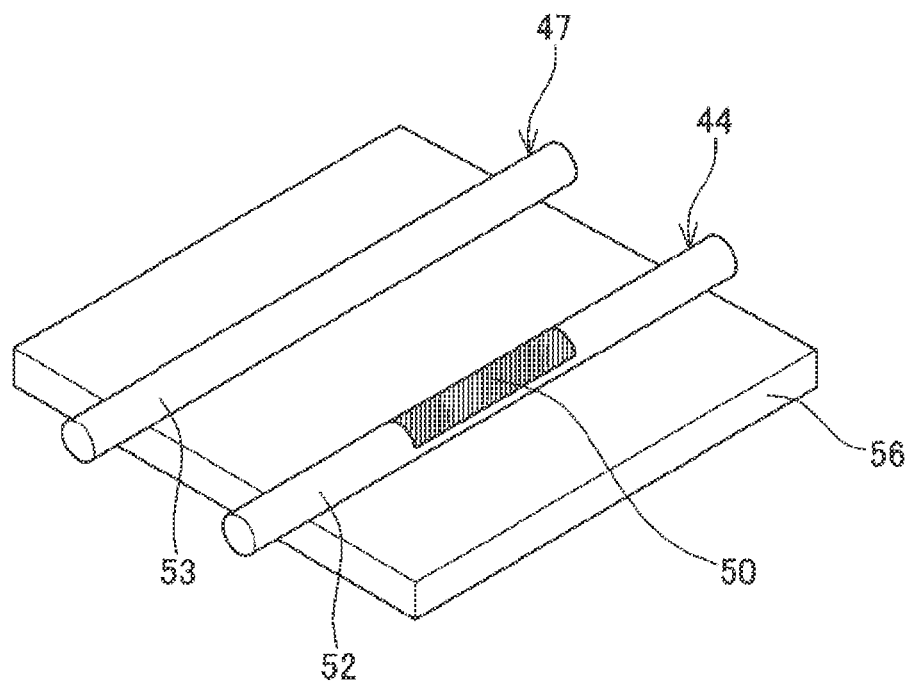
FIG. 7 is a diagram for explaining another embodiment of the present teachings, showing a state in which a detection optical fiber and compensation optical fiber are attached to a plate member.

As shown in FIG. 7, the fuel property determining apparatus of the present embodiment has a first optical fiber 44 and a second optical fiber 47. As with the first embodiment, in the first optical fiber 44 a part of the core 52 is exposed to fuel, and the gold thin film 50 is formed therein. Unlike the first optical fiber 44, in the second optical fiber 47 a part of a core 53 is exposed to the fuel but the gold thin film is not formed on the core 53. The light propagated through the first optical fiber 44 is received by a photodiode (not shown), and the light propagated through the second optical fiber 47 is also received by a photodiode (not shown). The first optical fiber 44 and the second optical fiber 47 are secured to a plate member 56.

An ECU of the present embodiment determines the refractive index of the fuel by using an output of the photodiode that receives the light propagated by the first optical fiber 44 (i.e., the intensity of the light propagated by the first optical fiber 44) and an output of the photodiode that receives the light propagated by the second optical fiber 47 (i.e., the intensity of the light propagated by the second optical fiber 47). Specifically, the intensity of the light propagated by the second optical fiber 47 is subtracted from the intensity of the light propagated by the first optical fiber 44, and then the refractive index of the fuel is determined from the subtraction. Because the first optical fiber 44 and the second optical fiber 47 are secured to the same plate member 56, the first optical fiber 44 and the second optical fiber 47 are deformed in the same manner. Therefore, by obtaining the difference between the outputs of the first optical fiber 44 and the second optical fiber 47, the change in the intensity of the light caused by the deformation of the first optical fiber 44 can be compensated. As a result, the refractive index (which correspondingly represents the alcohol concentration) of the fuel can be detected accurately.

Note that the LED causing the light to enter the first optical fiber 44 and the LED causing the light to enter the second optical fiber 47 can be the same LED. According to this configuration, even when the intensities of the light received by the photodiodes change due to temporal change or voltage change of the LED, the intensity of the light entering the first optical fiber 44 and the intensity of the light entering the second optical fiber 47 change in a similar manner, and thus the influence thereof can be canceled. Consequently, the refractive index of the fuel can be obtained with a high degree of accuracy. In this case, by disposing a switchable mirror in the incidence optical system, the state in which the light enters the first optical fiber 44 can be switched with the state in which the light enters the second optical fiber 47.

Moreover, the photodiode that receives the light propagated through the first optical fiber 44 and the photodiode that receives the light propagated through the second optical fiber 47 can be the same photodiode. According to this configuration, the influence of the temporal change of the photodiode can be canceled, and the refractive index of the fuel can be obtained accurately. In this case, by disposing a switchable mirror in the light receiving optical system, the state in which the light propagated through the first optical fiber 44 is guided to the photodiode can be switched with the state in which the light propagated through the second optical fiber 47 is guided to the photodiode. Alternatively, a switchable mirror may be disposed in the incidence optical system, so that the state in which the light enters the first optical fiber 44 is switched with the state in which the light enters the second optical fiber 47.

Fourth Embodiment

Next, a fuel property determining apparatus according to a fourth embodiment will be described. Unlike the fuel property determining apparatus of the first embodiment, the fuel property determining apparatus of the fourth embodiment further has a vapor pressure sensor for detecting the vapor pressure of fuel supplied to an engine, and determines the property of the fuel supplied to the engine based on the alcohol concentration detected by the alcohol concentration detection sensor and the vapor pressure detected by the vapor pressure sensor. The rest of the configuration is same as that of the first embodiment, and thus the overlapping description thereof is omitted.

Figure 8:
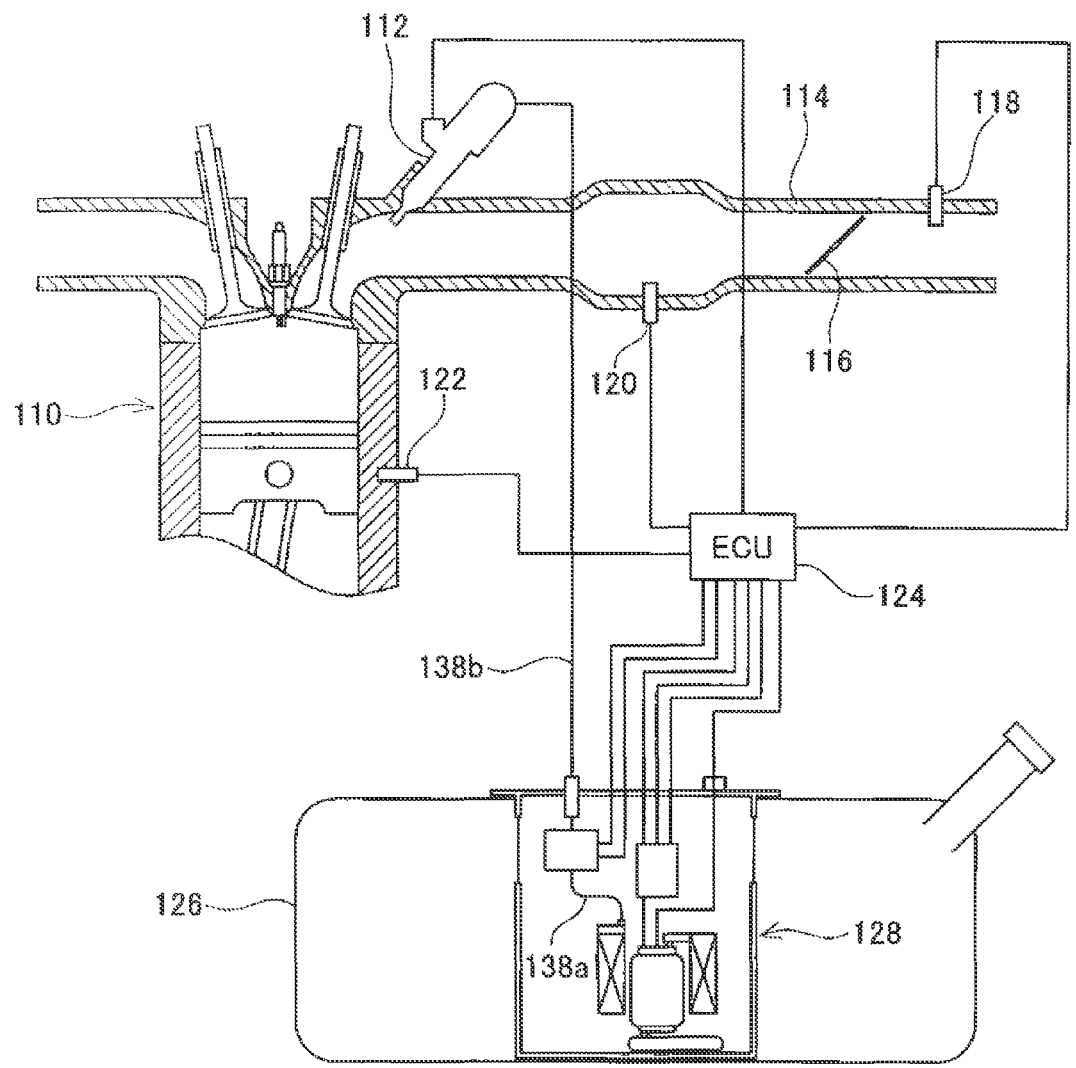
FIG. 8 is a diagram showing a configuration of a fuel supply system according to another embodiment of the present teachings.
Figure 9:
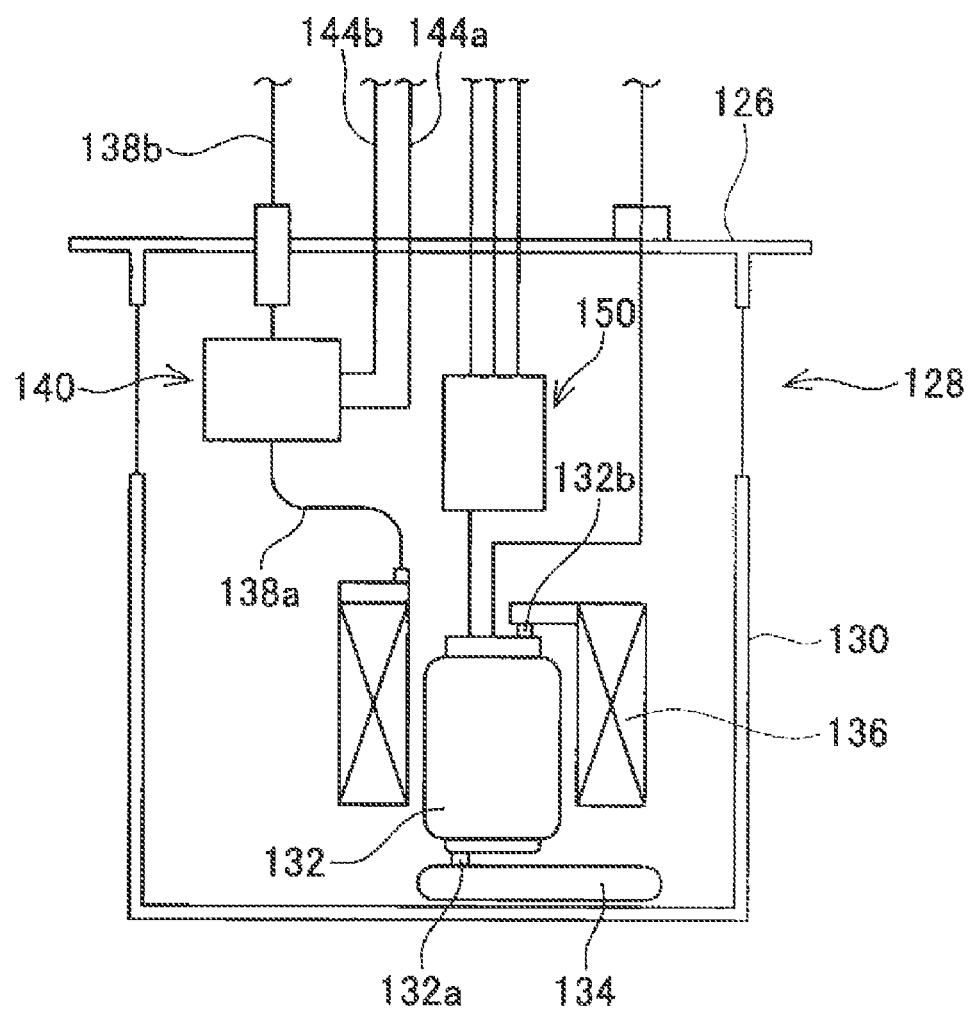
FIG. 9 is a diagram showing an enlargement of a configuration within a fuel tank provided to the fuel supply system shown in FIG. 8.

As shown in FIGS. 8 and 9, the fuel property determining apparatus of the fourth embodiment comprises an alcohol concentration detection sensor 140 for detecting the alcohol concentration of the fuel supplied to the engine, and a vapor pressure sensor 150 for detecting the vapor pressure of the fuel supplied to the engine. The alcohol concentration detection sensor 140 has the same configuration as that in the first embodiment. The vapor pressure sensor 150 is a sensor that detects the Reid vapor pressure of fuel. The vapor pressure sensor 150 can utilize a conventionally-known structure (e.g., Japanese Patent Application Publication No. H05-223723). The alcohol concentration detection sensor 140 and the vapor pressure sensor 150 are connected to an ECU 124.

An output of the alcohol concentration detection sensor 140 and an output of the vapor pressure sensor 150 are input to the ECU 124. The ECU 124 determines the property of the fuel supplied to the engine based on the output of the alcohol concentration detection sensor 140 and the output of the vapor pressure sensor 150. The ECU 124 will be described in detail with reference to FIGS. 10 to 13.

Figure 11:
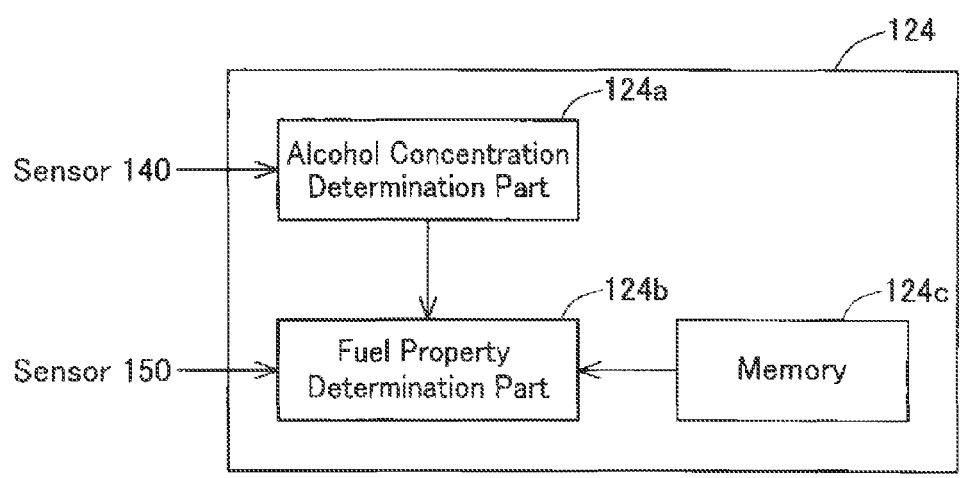
FIG. 11 is a diagram for explaining an internal structure of an ECU.

As shown in FIG. 11, the ECU 124 has an alcohol concentration determination part 124a, fuel property determination part 124b, and memory 124c. The alcohol concentration determination part 124a determines the alcohol concentration based on the output of the alcohol concentration detection sensor 140, as with the first embodiment. That is, the refractive index of the fuel supplied to the engine is specified from the output of the alcohol concentration detection sensor 140, and then the alcohol concentration of the fuel supplied to the engine is determined from this refractive index.

Figure 10:
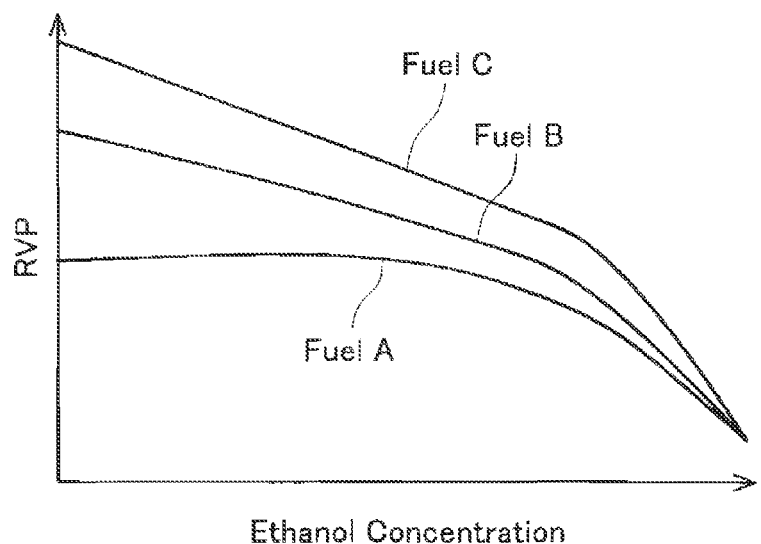
FIG. 10 is a diagram showing a relationship between the alcohol concentration of fuel and vapor pressure of the fuel (i.e., RVP).

The memory 124c stores a relationship of each of a plurality of predetermined fuels (i.e., fuels A, B, C in the present embodiment) having different heavy or light qualities. The relationship of each of the plurality of predetermined fuels is a relationship between the vapor pressure and the alcohol concentration. FIG. 10 shows the stored relationships of the vapor pressure and the alcohol concentration, where the vapor pressure is shown as a function of the alcohol concentration. In regards to the heavy/light gravity of the fuels, the fuel A has a high heavy/light gravity (so called heavy fuel). The fuel B has a medium heavy/light gravity (so called medium gravity fuel). The fuel C has a low heavy/light gravity (so called light fuel). As is clear from FIG. 10, the vapor pressure of the fuel becomes lower as the alcohol concentration (i.e., ethanol concentration) becomes higher. Furthermore, the vapor pressure of the fuel becomes lower as the heavy/light gravity (i.e., the ratio of the heavy fuel) becomes higher. Furthermore, in a region where the alcohol concentration is low, the vapor pressure of fuel changes less significantly. On the other hand, in a region where the alcohol concentration is high, the vapor pressure of the fuel changes significantly. Especially for the fuel A, in the region where the alcohol concentration is low, the vapor pressure of the fuel hardly changes, even when the alcohol concentration thereof changes. For this reason, it is difficult to accurately determine the alcohol concentration based only on the output of the vapor pressure sensor 150.

FIG. 12 shows an example of data stored in the memory 124c. As shown in FIG. 12, the memory 124c stores the vapor pressure ($a_0$, $a_{10}$, . . . , $a_{100}$) obtained when each alcohol concentration of the fuel A is 0%, 10%, . . . , 100%, the vapor pressure ($b_0$, $b_{10}$, . . . , $b_{100}$) obtained when each alcohol concentration of the fuel B is 0%, 10%, . . . , 100%, and the vapor pressure ($c_0$, $c_{10}$, . . . , $c_{100}$) obtained when each alcohol concentration of the fuel C is 0%, 10%, . . . , 100%. Here, the heavy/light gravity of the fuel A is a %, the heavy/light gravity of the fuel B is b %, and the heavy/light gravity of the fuel C is c %. Note that the data stored in the memory 124c is not limited to three types of data for the fuels A, B, C, and thus data of other types of fuels (e.g., fuels with different heavy or light qualities) may be stored as well. By increasing the number of fuel types stored in the memory 124c, the heavy/light gravity of the fuel that is the object of detection (which hereinbelow may be referred to as the "target fuel" relative to the plurality of predetermined fuels) can be determined with a high degree of accuracy.

The fuel property determination part 124b determines the heavy/light gravity of the fuel (target fuel) supplied to the engine based on the alcohol concentration determined by the alcohol concentration determination part 124a and the data stored in the memory 124c. That is, when the alcohol concentration is determined, vapor pressures a, b, c of the fuels A, B, C having the determined alcohol concentration are calculated based on the data stored in the memory 124c. For example, when the alcohol concentration is 25%, the vapor pressure of the fuel A can be $(a_{20}+a_{30})/2$ based on the vapor pressure $a_{20}$ obtained when the alcohol concentration of the fuel A is 20% and the vapor pressure $a_{30}$ obtained when the alcohol concentration is 30%. The vapor pressure of the fuel B and the vapor pressure of the fuel C can be calculated in the same way.

Once the vapor pressures of the fuels A, B, C are calculated, the heavy/light gravity of the fuel (target fuel) supplied to the engine is calculated from the calculated vapor pressures of the fuels A, B, C and the vapor pressure detected by the vapor pressure sensor 150. For example, suppose that the vapor pressure detected by the vapor pressure sensor 150 is p, and that the vapor pressure p is higher than the vapor pressure $a_p$ of the fuel A and lower than the vapor pressure $b_p$ of the fuel B (i.e., $a_p<p<b_p$). In this case, the heavy/light gravity of the fuel (target fuel) supplied to the engine can be calculated as a %+[(p−$ap_p$)/($b_p$−$a_p$)]×(b %−a %). That is, the heavy/light gravity of the fuel (target fuel) supplied to the engine is calculated by interpolating or extrapolating the data on the calculated vapor pressures of the fuels A, B, C. Note that, in order to control the engine, the property of fuel supplied to the engine may be determined based on the vapor pressure values themselves without obtaining the degree of the heavy/light gravity of the fuel (target fuel).

Figure 13:
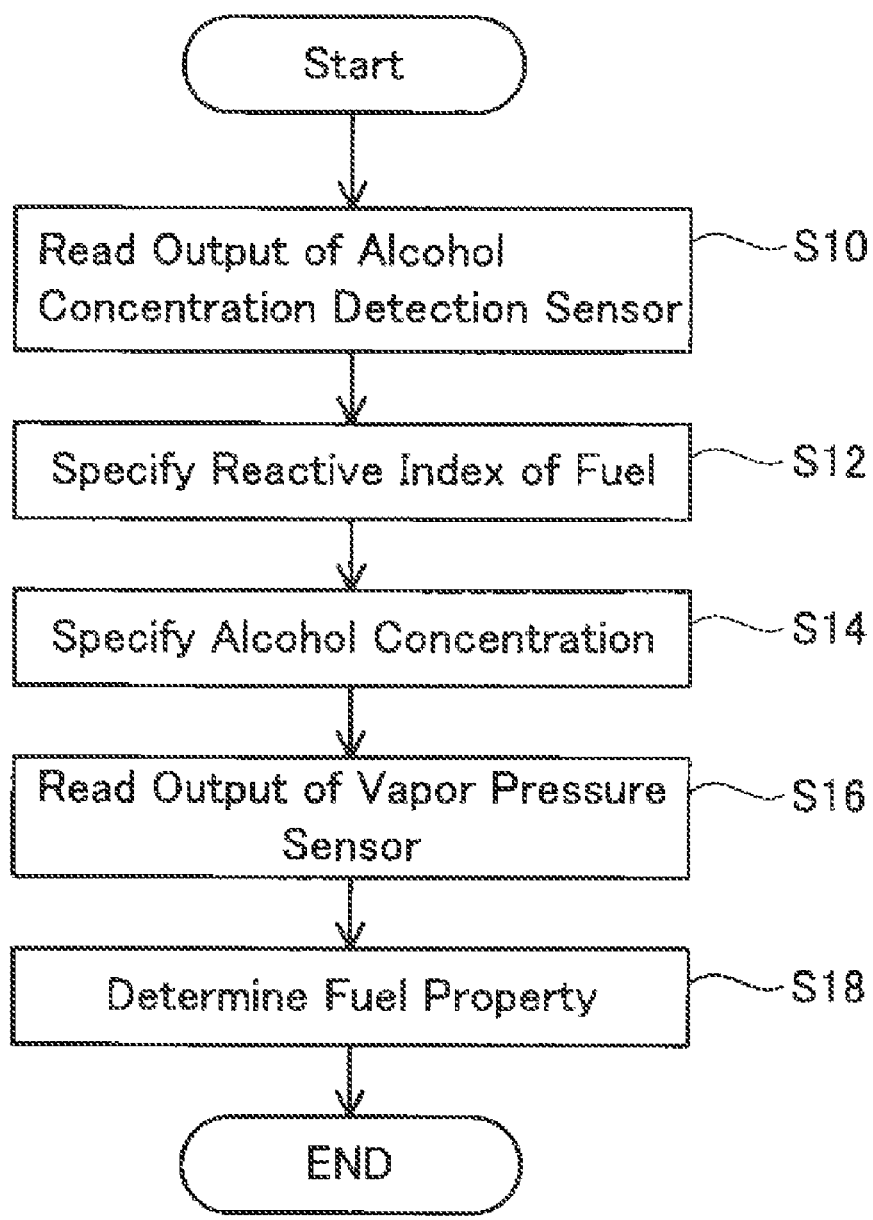
FIG. 13 is a flowchart of a process for determining the property of the fuel.

Next, the process of the ECU 124 for determining the property of fuel supplied to the engine will be described. As shown in FIG. 13, the ECU 124 first reads the output of the alcohol concentration detection sensor 140 (S10). In other words, the ECU 124 detects the intensities of the light received by the photodiodes (i.e., the light propagated through the cores of the optical fibers).

The ECU 124 then calculates the refractive index of fuel supplied to the engine from the output of the alcohol concentration detection sensor 140 (S12), and determines the alcohol concentration of the fuel supplied to the engine from this refractive index (S14). That is, the ECU 124 specifies the alcohol concentration based on the refractive index specified from the output of the alcohol concentration detection sensor 140 and the "refractive index—alcohol concentration" relationship stored in the memory 124c (FIG. 6). As is clear from FIG. 6, the "refractive index—alcohol concentration" properties of the fuels A, B, C are slightly, but not significantly, different from one another (especially the difference among the fuels A, B, C is emphasized in FIG. 6). Therefore, even when the heavy/light gravity of the fuel supplied to the engine is different from that of the predetermined fuel types, the alcohol concentration of the fuel supplied to the engine can be determined accurately from the refractive index calculated from the output of the alcohol concentration detection sensor 140.

Next, the ECU 124 reads the output of the vapor pressure sensor 150 (S16), and calculates the heavy/light gravity of the fuel supplied to the engine based on the output of the vapor pressure sensor 150, the alcohol concentration determined in step S14, and the "heavy/light gravity—vapor pressure" relationship stored in the memory 124c (S18). That is, first, the vapor pressure of each of the fuels A, B, C corresponding to the alcohol concentration determined in S14 is calculated based on the data stored in the memory 124c. Subsequently, the heavy/light gravity of the fuel supplied to the engine is calculated based on the calculated vapor pressure of each of the fuels A, B, C and the vapor pressure detected by the vapor pressure sensor 150. Once the alcohol concentration and the heavy/light gravity of the fuel supplied to the engine are determined by the process described above, the ECU 124 determines the amount of fuel injected to an engine 110 and the timing of injecting the fuel, based on the determined fuel property.

In the fuel property determining apparatus of the fourth embodiment, first the alcohol concentration is determined based on the output of the alcohol concentration detection sensor 140, and then the "heavy/light gravity—vapor pressure" relationship in the determined alcohol concentration is specified. Thereafter, the heavy/light gravity of the fuel is determined based on the output of the vapor pressure sensor 150. As described above, the alcohol concentration of the fuel can be detected without imposing a large influence on the heavy/light gravity thereof. In addition, the alcohol concentration detection sensor 140 has a good sensitivity, and the relationship between the output (i.e., refractive index) thereof and the alcohol concentration is linear. For this reason, the alcohol concentration detection sensor 140 can detect the alcohol concentration of the fuel accurately. Moreover, because the "heavy/light gravity—vapor pressure" relationship is specified based on the precisely detected alcohol concentration, and the heavy/light gravity of the fuel is specified from this relationship and the output of the vapor pressure sensor 150, the heavy/light gravity of the fuel can be calculated with a high degree of accuracy. Because the alcohol concentration and the heavy/light gravity of the fuel can be specified precisely, the property of the fuel can be determined accurately.

Note that the fuel property determining apparatus of each of the embodiments described above can be further provided with a temperature sensor for detecting the temperature of the fuel supplied to the engine. The ECU 24 (or 124) can correct the alcohol concentration (and/or the vapor pressure of the fuel) based on the fuel temperature detected by the temperature sensor. The fuel density is changed by the fuel temperature. When the fuel density changes as a function of temperature, the refractive index of the fuel changes accordingly. By correcting the alcohol concentration based on the fuel temperature detected by the sensor, the alcohol concentration of the fuel supplied to the engine can be determined accurately. Moreover, saturated vapor pressure of the fuel changes depending on the temperature. By correcting the vapor pressure based on the fuel temperature detected by the sensor, the vapor pressure of the fuel supplied to the engine can be detected with a high degree of accuracy.

In the fuel property determining apparatus of each of the embodiments, the section on the core 52 of the optical fiber 44 that is formed with the gold thin film 50 may be covered with a moisture separation membrane. By covering the gold thin film 50 with the moisture separation membrane, the influence of the moisture contained in the fuel can be reduced, and the alcohol concentration of the fuel can be determined accurately. A zeolite membrane, for example, can be used as the moisture separation membrane.

In addition, in the fuel property determining apparatus of each of the embodiments described above, the LED 42 and the photodiode 46 are disposed within the fuel flow path, but may be disposed outside the fuel flow path. According to this configuration, the LED 42 and the photodiode 46 are prevented from being immersed in the fuel, and thus fuel resistant performance thereof is no longer required. This can improve the reliability of the apparatus.

Finally, although the preferred embodiments have been described in detail, the present embodiments are merely for illustrative purpose only and are not restrictive. It is to be understood that various changes and modifications may be made without departing from the spirit or scope of the appended claims. In addition, the additional features and aspects disclosed herein may also be utilized singularly or in combination with the above aspects and features.

What is claimed is:

1. An apparatus, comprising;
a first sensor that detects a concentration of an alcohol contained in target fuel;
a second sensor that detects a vapor pressure of the target fuel;
a memory that stores first data for determining a "heavy/light gravity—vapor pressure" relationship based on the concentration of the alcohol; and
a processor that determines fuel property of the target fuel based on the first data stored in the memory, the alcohol concentration detected by the first sensor, and the vapor pressure detected by the second sensor.

2. The apparatus according to claim 1, wherein the processor (1) determines the "heavy/light gravity—vapor pressure" relationship based on the first data stored in the memory and the alcohol concentration detected by the first sensor, and (2) determines a heavy/light gravity of the target fuel based on the determined "heavy/light gravity—vapor pressure" relationship and the vapor pressure detected by the second sensor.

3. The apparatus according to claim 2, wherein
the first sensor outputs a signal to the processor, the signal corresponding to a refractive index of the target fuel, and
the processor determines the alcohol concentration of the target fuel based on the signal output from the first sensor.

4. The apparatus according to claim 3, wherein
the memory further stores second data representing a "refractive index—alcohol concentration" relationship of predetermined fuel having a predetermined heavy/light gravity, and
the processor determines the refractive index of the target fuel based on the signal output from the first sensor, and determines the alcohol concentration of the target fuel based on the determined refractive index and the second data.

5. The apparatus according to claim 4, wherein the processor determines the "heavy/light gravity—vapor pressure" relationship corresponding to the determined alcohol concentration.

6. The apparatus according to claim 5, wherein
the first data includes a "vapor pressure—alcohol concentration" relationship of each of a plurality of predetermined fuels having different heavy/light gravity,
the processor determines a vapor pressure of each of the plurality of predetermined fuels based on the first data and the determined alcohol concentration, and determines the heavy/light gravity of the target fuel based on the determined vapor pressure of each of the plurality of predetermined fuels and the vapor pressure detected by the second sensor.

7. The apparatus according to claim 6, wherein the processor calculates the heavy/light gravity of the target fuel by interpolating or extrapolating data on the determined vapor pressure of each of the plurality of predetermined fuels.

8. The apparatus according to claim 7, further comprising a third sensor that detects a temperature of the target fuel, wherein the processor corrects at least one of the detected alcohol concentration and the detected vapor pressure based on the temperature of the target fuel detected by the third sensor.

9. The apparatus according to claim 8, wherein the first sensor comprises a light source, a optical fiber, and a photodiode, wherein
the light source emits light,
the optical fiber is immersed in the target fuel, and propagates the light emitted by the light source to the photodiode, and
the photodiode receives the light propagated through the optical fiber.

10. The apparatus according to claim 9, wherein the optical fiber is configured to generate a surface plasmon resonance phenomenon when the optical fiber propagates the light emitted by the light source to the photodiode.

11. The apparatus according to claim 10, wherein the optical fiber includes a core and a thin film disposed on a surface of the core, wherein the core propagates the light to the photodiode, and the thin film causes the surface plasmon resonance phenomenon when the optical fiber propagates the light emitted by the light source to the photodiode.

12. The apparatus according to claim 3, wherein the first sensor comprises a light source, a optical fiber, and a photodiode, wherein
the light source emits light,
the optical fiber is immersed in the target fuel, and propagates the light emitted by the light source to the photodiode, and
the photodiode receives the light propagated through the optical fiber.

13. The apparatus according to claim 12, wherein the optical fiber is configured to generate a surface plasmon resonance phenomenon when the optical fiber propagates the light emitted by the light source to the photodiode.

14. The apparatus according to claim 13, wherein the optical fiber includes a core and a thin film disposed on a surface of the core, wherein the core propagates the light to the photodiode, and the thin film causes the surface plasmon resonance phenomenon when the optical fiber propagates the light emitted by the light source to the photodiode.

* * * * *